US00PP36432P2

(12) United States Plant Patent
Chauvet

(10) Patent No.: US PP36,432 P2
(45) Date of Patent: Feb. 11, 2025

(54) ***MUSA* PLANT NAMED 'Lou 1'**

(50) Latin Name: *Musa sikkimensis*
Varietal Denomination: Lou 1

(71) Applicant: Bruno Chauvet, Contres (FR)

(72) Inventor: Bruno Chauvet, Contres (FR)

( * ) Notice: Subject to any disclaimer, the term of this patent is extended or adjusted under 35 U.S.C. 154(b) by 0 days.

(21) Appl. No.: 18/582,616

(22) Filed: Feb. 20, 2024

(30) Foreign Application Priority Data

Nov. 3, 2023 (QZ) ..... PBR 2023/2304

(51) Int. Cl.
*A01H 5/12* (2018.01)
*A01H 6/00* (2018.01)

(52) U.S. Cl.
USPC ..... Plt./160

(58) Field of Classification Search
USPC ..... Plt./160
CPC ..... A01H 5/12; A01H 5/00; A01H 6/00
See application file for complete search history.

(56) References Cited

PUBLICATIONS

Crocus *Musa sikkimensis* Ever Red ('Lou 1'), retrieved on Jun. 24, 2024 at https://www.crocus.co.uk/plants/_/musa-sikkimensis-ever-red--lou-1/classid.2000050207/, 3 pp. (Year: 2024).*
Missouri Botanical Garden *Musa* 'Siam Ruby', retrieved on Jun. 25, 2024 at https://www.missouribotanicalgarden.org/PlantFinder/PlantFinder Details.aspx?taxonid=269092&isprofile=0&bt=4, 2 pp. (Year: 2024).*
YouTube video New for 2023: *Musa sikkimensis* Ever Red, retrieved on Jun. 24, 2024 at https://www.youtube.com/watch?v=Y4xJ_svgM9g, 2 pp. (Year: 2023).*

* cited by examiner

*Primary Examiner* — June Hwu
(74) *Attorney, Agent, or Firm* — Penny J. Aguirre

(57) ABSTRACT

A new cultivar of *Musa* plant named 'Lou 1' that is characterized by its leaves with olive green and maroon-red leaves stripes on both leaf surfaces that is retained until late summer, its good growth as both an indoor and outdoor plant, its good cold hardiness; at least in U.S.D.A. Zones 6 to 11, its high wind tolerance, and its late spring emergence in cold climates followed by a vigorous growth habit.

2 Drawing Sheets

Botanical classification: *Musa sikkimensis*.
Cultivar designation: 'Lou 1'.

CROSS-REFERENCE TO RELATED APPLICATIONS

This application claims priority to European Community Plant Variety Office (CPVO) Plant Breeder's Rights Application No. 2023/2304 filed on Nov. 3, 2023, under 35 U.S.C. 119(f), the entire contents of which is incorporated by reference herein. The Application is also related to European Community Plant Variety Office (CPVO) Plant Breeder's Rights Application No. 2019/1406 filed on Nov. 6, 2019; however, the application was withdrawn due to lack of plant material for testing. The information for the plant breeders' rights applications was received directly from the Inventor.

BACKGROUND OF THE INVENTION

The present invention relates to a new and distinct cultivar of *Musa sikkimensis* known as 'Lou 1', and is hereinafter referred to as 'Lou 1'. 'Lou 1' is a new cultivar of Darjeeling banana plant grown for container and landscape use.

'Lou 1' was discovered by the Inventor as a chance seedling growing in a container in a production greenhouse in Contres, France in 2016. The exact parentage is unknown; however, it is most likely a seedling of open pollinated 'Red Tiger' (not patented) based on its characteristics and its proximity to the new cultivar.

Asexual propagation of the new cultivar was first accomplished by division in Louzesse, France in 2016 by the Inventor. Asexual propagation by division and tissue culture using meristematic tissue has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Lou 1' as a new and unique cultivar of *Musa*.

1. 'Lou 1' exhibits leaves with olive green and maroon-red leaves stripes on both leaf surfaces that is retained until late summer.
2. 'Lou 1' exhibits good growth as both an indoor and outdoor plant.
3. 'Lou 1' exhibits good cold hardiness; at least in U.S.D.A. Zones 6 to 11.
4. 'Lou 1' exhibits high wind tolerance; at least in up to 30 miles an hour winds.
5. 'Lou 1' exhibits late spring emergence in cold climates followed by a vigorous growth habit.

'Red Tiger', a probable parent plant, is similar to 'Lou 1' in having foliage with red and green stripes. 'Red Tiger' differs from 'Lou 1' in having less distinguishable red stripes on the foliage (more blotchy) and in losing its red coloration earlier in summer. 'Lou 1' can be most closely compared to typical plants of the species *Musa basjoo* and *Musa acumi-*

*nata* 'Siam Ruby' (not patented). Typical plants of *Musa basjoo* differ from 'Lou 1' in having thicker foliage, foliage that lacks stripes, and lower wind resistance. *Musa* 'Siam Ruby' differs from 'Lou 1' in having thicker foliage that emerges green in spring and changes to red with chartreuse green stripes (brighter and less abundant than 'Lou 1') and less frost resistance.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plantipp (the breeder's representative for licensing), YouTube (Plantipp), A L'ombre des figuiers and Thompson & Morgan.

BRIEF DESCRIPTION OF THE DRAWINGS

The accompanying color photographs illustrate the overall appearance and distinct characteristics of the new *Musa*. The photographs were taken of a 3-month-old plant as grown indoors in a 17-cm container in Waddinxveen, Netherlands.

The photograph in FIG. 1 provides a side view of 'Lou 1'.

Figure 1:
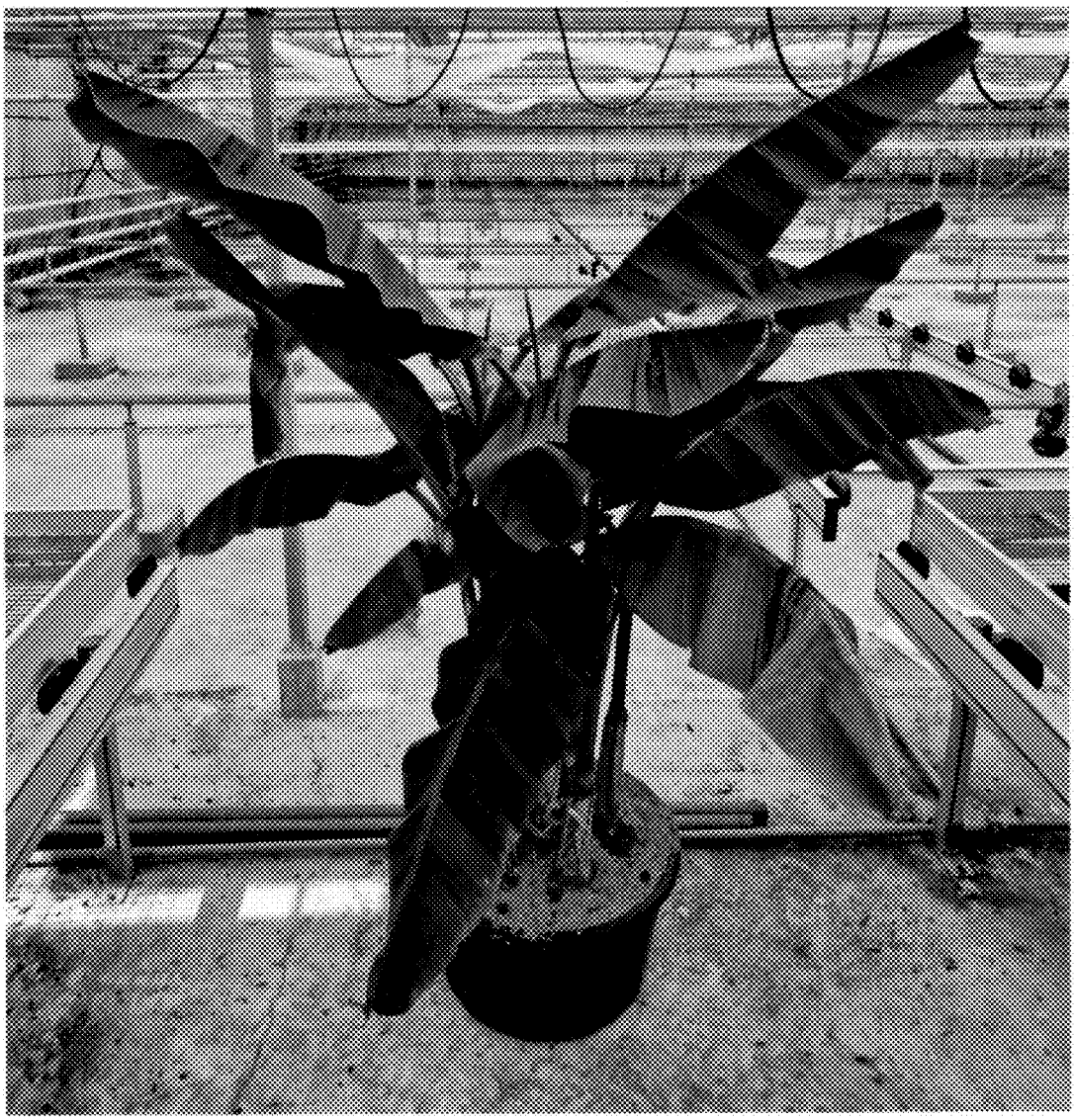
Figure 2:
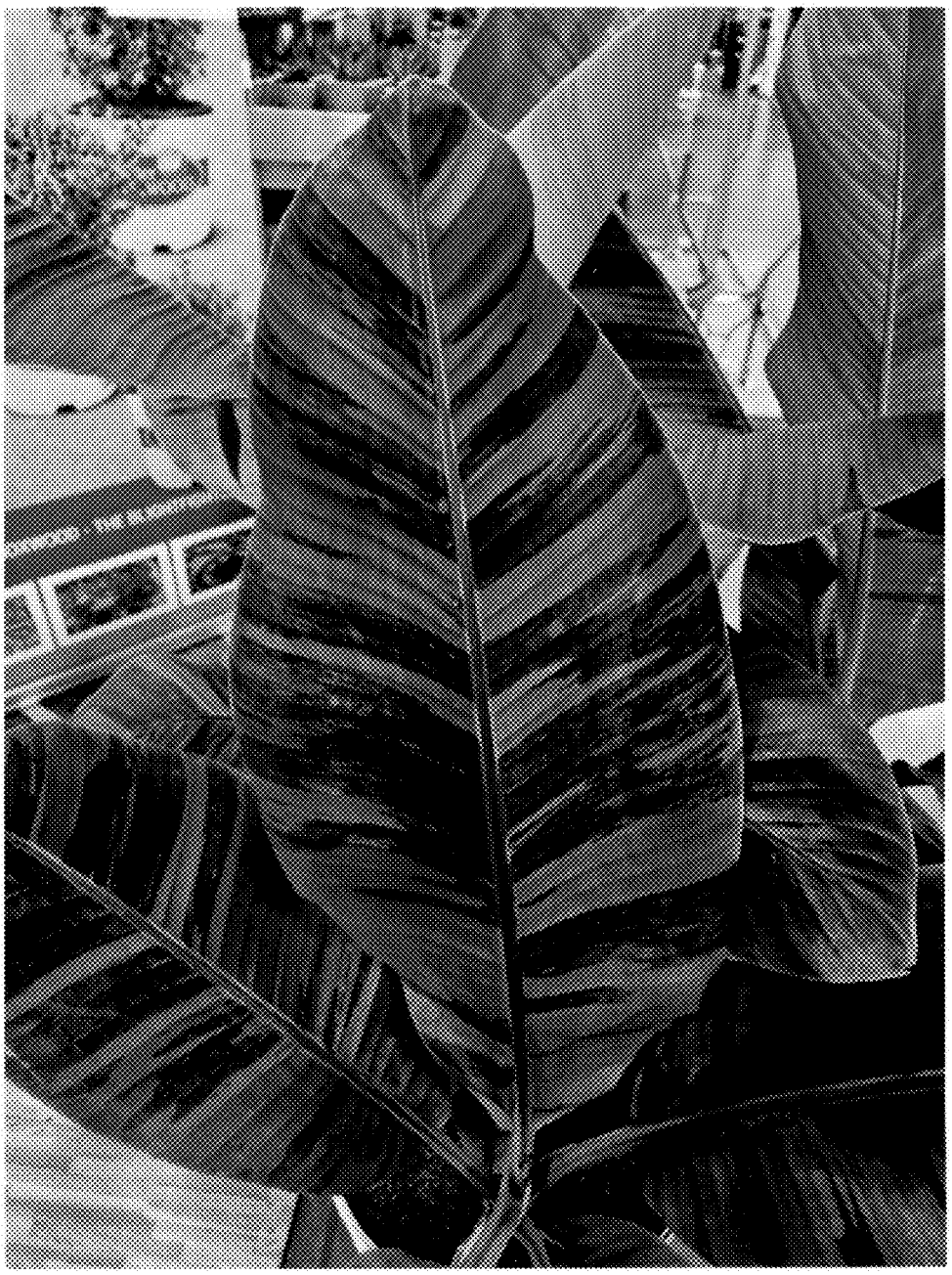

The photograph in FIG. 2 provides a close-up view of the foliage of 'Lou 1'.

The colors in the photographs are as close as possible with the digital photography and printing techniques utilized and the color codes in the detailed botanical description accurately describe the new *Musa*.

DETAILED BOTANICAL DESCRIPTION OF THE PLANT

The following is a detailed description of a 3-year-old plant of the new cultivar as grown indoors in a 4-L container in Waddinxveen, Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Tropical, tender perennial (deciduous or evergreen depending on climate), pseudostems arise annually from rhizomes in cold climates.

*Plant habit*.—Upright pseudostems with cascading, spreading leaves, tufted leaves producing thick stems from petioles (pseudostems).

*Height and spread*.—Average of 80 cm in height, 75 cm in width as a 3-month-old plant grown in a container.

*Hardiness*.—At least in U.S.D.A. Zones 6 to 11.

*Diseases and pests*.—No susceptibility or resistance to diseases or pests has been observed.

*Propagation type*.—Division and tissue culture.

*Roots*.—Fleshy with secondary fibrous roots, NN155A in color.

*Corms*.—None were observed to form on plants currently grown.

*Rhizomes*.—An average of 5 cm in length and 1.5 cm in width, NN155A and 162C in color.

*Other resistance*.—High wind resistance due to leaves that curve downward from midrib.

*Root development*.—Tissue culture; average of 8 weeks to produce a rooted 84-cell plug from stage, an 84-cell plug can finish directly in a 4-L container.

*Growth rate*.—Slow to emerge in spring then vigorous.

Trunk description (pseudostem):

*Stem size*.—An average of 42 cm in length and 2.3 cm in width (with sheaths).

*Stem type*.—Strong, round in shape, surrounded by sheathed leaf petioles.

*Stem color*.—146C to 146D and 185A.

*Stem surface*.—Smooth and glossy.

*Internode*.—10 cm.

Foliage description:

*Leaf size*.—55 cm in length and 25 cm in width.

*Leaf shape*.—Broadly lanceolate.

*Leaf division*.—Simple.

*Leaf base*.—Rounded.

*Leaf apex*.—Acute.

*Leaf venation*.—Pinnately parallel, mid rib is sulcate, upper surface 187B, lower surface 187A.

*Leaf margins*.—Entire, slightly undulating.

*Leaf attachment*.—Petiolate.

*Leaf arrangement*.—Alternate with petioles sheathed.

*Leaf surface*.—Both upper and lower surfaces are glabrous with slight glossiness.

*Leaf color*.—Young upper surface; 146C, striped 187B, young lower surface; 146A to 146B, striped 187B, mature upper surface; 147A to 147B, striped 187A to 187B, mature lower surface; 147A, striped 187A to 187B, striping is variable, but average about 30% of the leaf surfaces with the stripes ranging from 2 mm to 6 cm in width.

*Leaf size*.—Average of 55 cm in length and 25 cm in width.

*Petioles*.—4.5 cm in length, 1.8 cm in diameter, color; 146C to 146D and 187B to 187C, the attitude of the petiole wings at base are primarily straight but occasionally curved outwards.

Inflorescence description: No flowers have been observed by the Inventor, not even on the original plant.

Fruit and seed: No fruit has not been observed by the Inventor, not even on the original plant.

It is claimed:

1. A new and distinct cultivar of *Musa* plant named 'Lou 1' as herein illustrated and described.

* * * * *